(12) United States Patent
Callaway et al.

(10) Patent No.: US 10,843,986 B2
(45) Date of Patent: Nov. 24, 2020

(54) METHOD FOR REDUCING THE OXYGENATE CONTENT OF A HYDROCARBON PROCESS STREAM TREATED WITH OR CONTAINING AN OXYGENATE

(71) Applicant: Caltech Global Enterprises, LLC, Sapulpa, OK (US)

(72) Inventors: Michael D. Callaway, Sapulpa, OK (US); William Jay Turner, Seabrook, TX (US)

(73) Assignee: CALTECH GLOBAL ENTERPRISES, LLC, Sapulpa, OK (US)

( * ) Notice: Subject to any disclaimer, the term of this patent is extended or adjusted under 35 U.S.C. 154(b) by 0 days.

(21) Appl. No.: 16/507,882

(22) Filed: Jul. 10, 2019

(65) Prior Publication Data
US 2020/0017428 A1    Jan. 16, 2020

Related U.S. Application Data

(60) Provisional application No. 62/696,176, filed on Jul. 10, 2018.

(51) Int. Cl.
*C07C 7/12* (2006.01)
*C10G 25/00* (2006.01)

(52) U.S. Cl.
CPC .............. *C07C 7/12* (2013.01); *C10G 25/003* (2013.01); *C10G 2300/202* (2013.01)

(58) Field of Classification Search
CPC .. B01D 2251/604; B01D 53/02; B01D 53/52; B01D 53/81; B01J 20/06; B01J 20/28004; B01J 20/2803; B01J 20/3021; B01J 20/3042; B01J 20/3078; B01J 20/3085; B01J 2220/4868; B01J 20/041
See application file for complete search history.

(56) References Cited

U.S. PATENT DOCUMENTS

| 8,404,031 B1 | 3/2013 | Callaway |
| 8,759,252 B1 | 6/2014 | Callaway |
| 2004/0254416 A1* | 12/2004 | Risch ........................ C07C 7/12 585/824 |

FOREIGN PATENT DOCUMENTS

WO    2018067990 A1    4/2018

OTHER PUBLICATIONS

O'Brien et al, "Adjusting Gas Treatment Strategies to Resolve Methanol Issues", Aug. 2016, Publisher: www.digitalrefining.com.

* cited by examiner

*Primary Examiner* — Sharon Pregler
(74) *Attorney, Agent, or Firm* — Gable Gotwals

(57) ABSTRACT

A method of this disclosure for removing oxygenates from a hydrocarbon process stream includes passing the hydrocarbon process stream through a vessel containing a mixed metal oxide having an amorphous non-crystalline structure and containing a metal in at least two oxidation states in a hydrate form, the hydrocarbon process stream having a first oxygenate content when entering the vessel and a second lower oxygenate content when exiting the vessel. The hydrocarbon stream may be a gas or a liquid stream.

22 Claims, No Drawings

METHOD FOR REDUCING THE OXYGENATE CONTENT OF A HYDROCARBON PROCESS STREAM TREATED WITH OR CONTAINING AN OXYGENATE

CROSS-REFERENCE

This application claims priority to U.S. 62/696,176, filed Jul. 10, 2018.

BACKGROUND

This disclosure is in the field of systems and processes designed to remove oxygenates such as methanol added to hydrocarbon process streams such as natural gas, propane, and butane.

Hydrocarbon process streams contain various oxygenates, some of which are introduced by production/process chemicals used in the industry. In C1 to C10 hydrocarbon matrices, for example, the following oxygenates may be found: acetaldehyde, acetone, allyl alcohol, isobutanol, tert-butyl alcohol, sec-butanol, butylaldehyde, diethyl ether, dimethyl ether, ethyl tert-butyl ether, ethanol, isobutylaldehyde, isovaleraldehyde, 2-butatone (MEK), methanol, methyl tert-butyl ether, N-butanol, N-propyl alcohol and isopropanol, propanols, propionaldehde, propyl ether, tert-amyl alcohol, tertiary amyl methyl ether (TAME), and valeraldehyde.

By way of a non-limiting example, methanol is commonly introduced into hydrocarbon process streams as either a hydrate inhibitor, freeze point depressant, or as an additive blended with sour gas ($H_2S$) scavengers. See D. O'Brien et al., *Adjusting Gas Treatment Strategies to Resolve Methanol Issues*, Laurance Reid Gas Conditioning Conference (Norman, Okla., Feb. 21-24, 2016), the content of which is hereby incorporated by reference. While the methanol can be recovered in liquid knockout drums, a portion of it remains in the hydrocarbon process stream. As methanol use increases at the production end, and as natural gas shippers continue to impose stringent methanol limits at the consumer end, midstream operators are challenged with reducing methanol levels.

Shippers that contract for hydrocarbon gases or liquids typically specify a limit as to the amount of oxygenates that can be present. In some cases, this amount remains above the specified or predetermined limit and the gas or liquid is labeled as "off-spec." Additionally, as the limit becomes more stringent, the difficulty of achieving increases disproportionately. For example, reducing an inlet stream containing 10 ppm to less than 0.5 ppm is significantly more difficult than a 10 ppm reduction if the inlet stream contained 210 ppm of oxygenates. A typical oxygenate limit may be no more than 200 ppm or no more than 50 ppm. Some midstream operators may not have equipment or methods to detect levels below 50 ppm.

SUMMARY

A method of this disclosure for removing oxygenates from a hydrocarbon process stream includes passing the hydrocarbon process stream through a vessel containing a mixed metal oxide having an amorphous non-crystalline structure and containing a metal in at least two oxidation states in a hydrate form, the hydrocarbon process stream having a first oxygenate content when entering the vessel and a second lower oxygenate content when exiting the vessel. The mixed metal oxide may be non-magnetic. The mixed metal oxide may include a crystalline structure in an amount less than that of the amorphous non-crystalline structure. In some embodiments an amount of the metal in one oxidation state is different than an amount of the metal in another oxidation state. The metal may be manganese, iron, nickel, copper, zinc, alumina, vanadium, titanium, magnesium, or molybdenum.

The oxygenate may be one found in C1 to C10 hydrocarbon matrices. For example, acetaldehyde, acetone, allyl alcohol, isobutanol, tert-butyl alcohol, sec-butanol, butylaldehyde, diethyl ether, dimethyl ether, ethyl tert-butyl ether, ethanol, isobutylaldehyde, isovaleraldehyde, 2-butatone (MEK), methanol, methyl tert-butyl ether, N-butanol, N-propyl alcohol and isopropanol, propanols, propionaldehde, propyl ether, tert-amyl alcohol, tertiary amyl methyl ether (TAME), and valeraldehyde. In some embodiments, the oxygenate includes methanol. In other embodiments, the oxygenate includes acetone and methanol.

The hydrocarbon process stream being treated by a material of this disclosure may be a gas or a liquid C1 to C10 hydrocarbon process stream. By way of a non-limiting example, the liquid may be an NGL mix, C2 to C6+.

The process stream may have been treated upstream of a vessel containing the material of this disclosure to reduce sour gas ($H_2S$) to a predetermined acceptable limit or level. The process stream may also have been one treated upstream of the vessel to reduce oxygenates to a first predetermined acceptable level, the vessel containing the material further reducing the oxygenate content of the process stream to a second lower predetermined acceptable level.

DETAILED DESCRIPTION

Embodiments of a scavenger material of this disclosure reduces by solvation the oxygenate content of a hydrocarbon process stream treated with an oxygenate. The scavenger material may be located in a treatment vessel of a midstream processing operation. In some embodiments, the scavenger material is located downstream of the midstream processing operation and upstream of an end user process. The oxygenate may be one typically found in a C1 to C10 hydrocarbon matrices, for example, acetaldehyde, acetone, allyl alcohol, isobutanol, tert-butyl alcohol, sec-butanol, butylaldehyde, diethyl ether, dimethyl ether, ethyl tert-butyl ether, ethanol, isobutylaldehyde, isovaleraldehyde, 2-butatone (MEK), methanol, methyl tert-butyl ether, N-butanol, N-propyl alcohol and isopropanol, propanols, propionaldehde, propyl ether, tert-amyl alcohol, tertiary amyl methyl ether (TAME), and valeraldehyde. In some embodiments, the oxygenate includes acetone and methanol. In other embodiments, the oxygenate is methanol.

The scavenger material may include a sorbent containing a composition of a mixed metal oxide, the metal being in various oxidation states including an oxyhydroxide. The material and mixed metal oxide may be non-magnetic. The material may be used to react with other gases such as, but not limited to sour gas ($H_2S$). Sour gas capture can take place upstream or downstream of, or concurrent with, the methanol removal. However, testing shows a material of this disclosure prefers to react to with $H_2S$ when $H_2S$ content is high relative to oxygenate content and to solvate where oxygenate content is high relative to $H_2S$ content. A scavenger material disclosed in WO 2018/067990 A1, the content of which is incorporated by reference herein, is a suitable material for use in a method of this disclosure.

In embodiments, the metal of the mixed metal oxide is manganese, iron, nickel, copper, or zinc in two or more oxidized states in hydrate form. In some embodiments, the mixed metal oxide may be alumina, vanadium, titanium, magnesium, or molybdenum in two or more oxidized states in hydrate form. In other embodiments the sorbent includes a first metal oxide and a second different metal or mixed metal oxide in hydrate form. The first and second different metals may be manganese, iron, nickel, copper, zinc, alumina, vanadium, titanium, magnesium, or molybdenum in at least two oxidation states.

The scavenger material may be synthesized from a metal precursor salt, neutralized and dried, and then washed or soaked to remove one or more byproducts. The resulting sorbent is a mixture of crystalline and amorphous structure and is in nanoparticulate form In embodiments, the characteristic structure may contain various percentages of amorphous structure. For example, the sorbent may have at least some amorphous structure like that disclosed in U.S. Pat. Nos. 8,404,031 B1 and 8,759,252 B1 to Callaway, the content of each is hereby incorporated by reference. The same is true of embodiments in which the sorbent includes a first and a second different metal oxide. The nanoparticle may be on the surface, with the sorbent being in cluster form.

During synthesis, the material may be in an intermediate form or final form after drying. The intermediate or final forms may be any shape preferable, including but not limited to briquetted, extrudate, granular, pellet, or spherical. In some embodiments, the scavenger material is washed or soaked and then dried.

Embodiments of the scavenger nanomaterial can be made using ferric or ferrous chloride salts neutralized with a base such as calcium hydroxide or its equivalent, formed in intermediate or final form and dried, and then washed or soaked to remove one or more byproducts such as salts.

In one embodiment, the metal is iron and the mixed metal oxide includes ferrous and ferric oxide, ferrous and ferric hydroxide, and ferric oxyhydroxide. In some embodiments, the ferric content is greater than the ferrous content. In other embodiments, the ferrous content is greater than the ferric content. In yet other embodiments, the hydroxide content is greater than the oxide content, oxyhydroxide content, or the total oxide and oxyhydroxide content. The mixed iron oxide may include just two oxidation states.

In some embodiments, the metal is manganese and the mixed metal oxide includes manganese oxides, manganese hydroxides, and manganese oxyhydroxides. In other embodiments, the metal is nickel and the mixed metal oxide includes nickel oxide, nickel hydroxide, and nickel oxyhydroxide. In yet other embodiments, the metal is copper and the mixed metal oxide includes copper oxides and copper hydroxide or includes zinc oxide and zinc hydroxide. Similar to the iron-based composition, these other compositions may have one form of the metal greater than another form or a greater content of one oxidation state than another oxidation state.

In embodiments, ferrous chloride is used as the precursor salt to make the scavenger material. In other embodiments, ferric chloride may be used as the precursor salt. The ferric chloride-produced scavenger material is harder, more dense, and more water-resistant than the ferrous-chloride embodiments. The ferrous chloride-produced embodiments, while more amenable to regeneration, tend to be softer, less dense, and less water-resistant. However, the ferrous chloride embodiments are more amenable to regeneration than the ferric chloride embodiments.

Regardless of whether ferric- or ferrous chloride precursor salt is used, the resulting scavenger nanomaterial includes an amorphous non-crystalline structure. Ferrous and ferric oxide, hydroxide, and oxyhydroxide crystalline structures may be present in combination with the amorphous non-crystalline structure.

The content of the scavenger material may be measured using means known in the art such as but not limited to X-ray diffraction analysis or energy dispersive X-ray analysis. In some embodiments, the material includes one or more metals different than that of metal of the mixed metal oxide. For example, a mixed iron oxide embodiment may include manganese, nickel, copper, zinc, or some combination thereof. Similarly, a mixed manganese metal oxide may include iron, nickel, copper, zinc, or some combination thereof. These other metals may be found in trace amounts upwards to 5% wgt., 10% wgt., or 15% wgt.

In some embodiments, the mixed metal oxide in various oxidation states and forming this amorphous non-crystalline structure of the material is in a range of 10% wgt. to 80% wgt. In other embodiments, the amorphous constituent is in a range of 10% wgt. to 20% wgt., 20% wgt. to 30% wgt., 30% wgt. to 40% wgt., 40% wgt. to 50% wgt, 50% wgt. to 60% wgt., 60% wgt. to 70% wgt., or 70% wgt. to 80% wgt, there being sub-ranges within these broader ranges In yet other embodiments, the amorphous constituent includes a range spanning two or more of the amorphous constituent ranges listed here.

The particle size of the scavenger material is less than 1,000 nm. In some embodiments, the particle size is less than 500 nm. In other embodiments, the particle size is less than 100 nm or less than 50 nm. In yet other embodiments, the particle size is less than 25 nm or 15 nm. The particle size may be in a range of 10 nm to 20 nm, 20 nm to 30 nm, 30 nm to 40 nm, 40 nm to 50 nm, 50 nm to 60 nm, 70 nm to 80 nm, 80 nm to 90 nm, 90 nm to 100 nm, 100 nm to 200 nm, 200 run to 300 run, 300 nm to 400 nm, 400 nm to 500 nm. In yet other embodiments, the particle size includes two or more of the particle size sub-ranges listed here, there being sub-subranges as well.

The surface area may be in a range of 50 $m^2/g$ to 500 $m^2/g$. In some embodiments, the average surface area is in a range of 50 $m^2/g$ to 100 $m^2/g$, 100 $m^2/g$ to 150 $m^2/g$, 150 $m^2/g$ to 200 $m^2/g$, 200 $m^2/g$ to 250 $m^2/g$, 250 $m^2/g$ to 300 $m^2/g$, 300 $m^2/g$ to 350 $m^2/g$, 350 $m^2/g$ to 400 $m^2/g$, 400 $m^2/g$ to 450 $m^2/g$, or 450 $m^2/g$ to 500 $m^2/g$. In yet other embodiments, the average surface area includes two or more of the surface area sub-ranges listed here, there being sub-subranges as well.

The material may be in any form preferable. In some embodiments, the porosity of the material (in its amorphous structure) in the loaded bed is in a range of 40% to 60% (meaning, for example, that a vessel having 100% of its total volume filled with the scavenger material may also contain 50% of its volume in water). In other embodiments, the porosity of the material is in a range of 45% to 55%. The water pore volume may be in a range of 0.20 ml/g to 0.25 ml/g, 0.21 ml/g to 0.24 ml/g, 0.22 ml/g to 0.23 ml/g. The water pore volume may be 0.23 ml/g.

The method may be run at pressures above the vapor pressure of the liquid hydrocarbon stream being treated. The method may also be run at ambient temperatures or process condition temperatures. For example, the method may be run at process conditions used for C2 to C6+ as typically found in NGL mixes. For C6 to C10+, without sufficient temperature (as indicated by viscosity value) the hydrocarbon can get trapped in the pores of the material. In embodiments, the temperature is above 32° F. (0° C.) and no greater than 800° F. (426° C.), there being sub-ranges within this overall range. In other embodiments, the temperature is less than 100° F. (38° C.). In yet other embodiments, the temperature is in a range of 60° F. to 80° F. (16° C. to 27° C.).

In embodiments, for liquid process streams the pressures and temperatures are those that maintain the stream in liquid form. By way of a non-limiting example, the process conditions for propane may be in a range of about 250 psig (again depending on the temperature); for butane the pressure may be in a range of about 400 psig (again, depending on the temperature). The pressure forces the liquid or gas into and out of the pores of the material, the solvation likely taking place in the surface area provided by the cluster. Under typical process conditions, no methoxide or methane is produced from, for example, the methanol but could be under other process conditions.

In a test of an embodiment of the method, a hydrocarbon gas stream comprising 200 ppm methyl alcohol and nitrogen was flowed at a rate of 350 ml/min at 5 psi and ambient temperature (59° F. to 77° F.; 15° C. to 25° C.) through a half-inch reaction vessel containing 20 ml of an oxyhydroxide embodiment of scavenger material. The gas stream measured 28 ppm methane at the inlet and 172 ppm methane at the outlet, about a 600% increase relative to the inlet methane content. Rather than absorb or adsorb the methanol, the scavenger material appeared to convert the methanol to methane. It is contemplated that under certain reaction conditions the methanol may be converted to methane, including the addition of additional reactants such as hydrogen and variation of process conditions such as temperature, pressure, flow rate, and time.

Samples of vapor (nitrogen matrix) and butane were passed through a scavenger material of this disclosure and analyzed for oxygenates following ASTM method D7423, Standard Test Method for Determination of Oxygenates in C2, C3, C4, and C5 Hydrocarbon Matrices by Gas Chromatography and Flame Ionization Detection. This test method covers the gas chromatographic procedure for the quantitative determination of organic oxygenates in C2, C3, C4, and C5 matrices by multidimensional gas chromatography and flame ionization detection. This test method is applicable when the hydrocarbon matrices have a final boiling point not greater than 200° C. The linear working range for oxygenates is 0.50 mg/kg to 100 mg/kg (or 0.50 ppm to 100 ppm). The tests conditions, procedures, and results are found in Table 1 below.

TABLE 1

Conditions: Ambient Temp: 80 deg F.; Humidity: 88%;
Dew Pt: 76 deg F. Procedure: Loading: 20 ml screened <1.4 mm;
Flow rate 1: scale 30.674 ml/min); Flow rate 2: scale 15.337 ml/min;
GHSV: 2022 hr-1

| Source and Feed | Sample | Scale | Sample time start | Sample time end | Oxygenates[1] measured at outlet |
|---|---|---|---|---|---|
| 8 Feed without Water. Dry Feed (methanol at inlet at 50.3 ppm) | 1 | 30 | 5 | 10 | >0.5 ppm |
|  | 2 | 15 | 5 | 15 | >0.5 ppm |
|  | 3 | 30 | 20 | 25 | >0.5 ppm |
|  | 4 | 15 | 30 | 40 | >0.5 ppm |
|  | 5 | 30 | 40 | 45 | >0.5 ppm |
| 6 Feed with Water (methanol at inlet at 5.8 ppm) | 7 | 30 | 40 | 45 | >0.5 ppm |

TABLE 1-continued

Conditions: Ambient Temp: 80 deg F.; Humidity: 88%;
Dew Pt: 76 deg F. Procedure: Loading: 20 ml screened <1.4 mm;
Flow rate 1: scale 30.674 ml/min); Flow rate 2: scale 15.337 ml/min;
GHSV: 2022 hr-1

| Source and Feed | Sample | Oxygenates[2] measured at outlet |
|---|---|---|
| 9 Liquid Butane (acetone at inlet 8.5 ppm; methanol at inlet 367 ppm) | 8 hr | >0.5 ppm |
|  | 16 hr | >0.5 ppm[3] |
|  | 24 hr | >0.5 ppm |

[1]acetaldehyde, acetone, butyldehyde, dimethyl ether, ethyl tert-butyl ether, ethanol, isobuyladehyde, methanol, methyl tert-buytl ether, n-propyl alcohol and isopropanol, propionaldehyde
[2]acetaldehyde, acetone, allyl alcohol, isobutanol, tert-butyl alcohol, sec-butanol, butylaldehyde, diethyl ether, dimethyl ether, ethyl tert-butyl ether, ethanol, isobutylaldehyde, isovaleraldehyde, 2-butatone (MEK), methanol, methyl tert-butyl ether, N-butanol, N-propyl alcohol and isopropanol, propanols, propionaldehde, propyl ether, tert-amyl alcohol, tertiary amyl methyl ether (TAME), and valeraldehyde
[3]acetone at less than 0.5 ppm at 8 hours, 3.7 ppm at 16 hour, less than 0.5 ppm at 24 hours.

Rather than react with the oxygenate, the scavenger material may bond or attract the polar bond of the oxygenate, with the bond or attraction, and therefore efficiency of removal, increasing with the polarity of the oxygenate. To test this theory, X-ray diffraction ("XRD") analysis and Fourier Transform Infrared ("FTIR") analysis was conducted on fresh and spent scavenger material of this disclosure. The fresh and spent scavenger material comprised 49% wgt. $Fe_3O_4$ and 15% wgt. $Fe_2O_3$. According to the FTIR analysis there is no methoxy functional group present in the spent catalyst after evaporation of the methanol. As for the XRD analysis the profiles of the fresh and spent samples were substantially similar. This would suggest that there is not a new chemical bond forming and the interaction of the oxygenate with the material is likely either a physical interaction or another attractive force acting on the oxygenated species. In embodiments of the method, the space velocity may be 2 or less, in a range of 1 to 2, 1.1 to 1.9, 1.2 to 1.8, 1.3 to 1.7, 1.4 to 1.6, or 1.5. The oxygenate level of the inlet stream may be 1000 ppm, 900 ppm, 800 ppm, 700 ppm, 600 ppm, 500 ppm, 400 ppm, 300 ppm, 200 ppm, 100 ppm, 90 ppm, 80 ppm, 70 ppm 60 ppm, 50 ppm, 40 ppm, 30 ppm, 20 ppm, 10 ppm, 5 ppm, or 0.5 ppm to 5 pm. The material may be regenerated by flowing a fast moving gas through the column, thereby breaking the polar bond, and the oxygenate reclaimed through means known in the art.

While embodiments of this disclosure have been described, the invention is defined by the following claims, including the full range of equivalents to which recited element or step of the claim is entitled.

What is claimed:

1. A method for reducing a methanol content of a hydrocarbon process stream treated with, and containing, methanol, the method comprising:
  passing the hydrocarbon process stream containing the methanol through a vessel containing a non-magnetic mixed metal oxide, hydroxide, and oxyhydroxide sorbent nanomaterial including an amorphous non-crystalline structure and containing a metal in at least two oxidation states in a hydrate form;
  the hydrocarbon process stream having a first methanol content when entering the vessel and a second lower methanol content when exiting the vessel.

2. A method for reducing a oxygenate content of a hydrocarbon process stream containing an oxygenate, the method comprising:

passing the hydrocarbon process stream containing the oxygenate through a vessel containing a non-magnetic mixed metal oxide, hydroxide, and oxyhydroxide sorbent nanomaterial including an amorphous non-crystalline structure and containing a metal in at least two oxidation states in a hydrate form;

the hydrocarbon process stream having a first oxygenate content when entering the vessel and a second lower oxygenate content when exiting the vessel.

3. The method of claim 2, the oxygenate including methanol.

4. The method of claim 2, the oxygenate including acetone.

5. The method of claim 2, the hydrocarbon process stream including a gas hydrocarbon.

6. The method of claim 2, the hydrocarbon process stream including a liquid hydrocarbon.

7. The method of claim 6, the hydrocarbon process stream including ethane.

8. The method of claim 6, the hydrocarbon process stream including propane.

9. The method of claim 6, the hydrocarbon process stream including butane.

10. The method of claim 6, the hydrocarbon process stream including pentane.

11. The method of claim 6, the hydrocarbon process stream including hexane.

12. The method of claim 2, the oxygenate including at least one oxygenate selected from the group consisting of acetaldehyde, acetone, allyl alcohol, isobutanol, tert-butyl alcohol, sec-butanol, butylaldehyde, diethyl ether, dimethyl ether, ethyl tert-butyl ether, ethanol, isobutylaldehyde, isovaleraldehyde, 2-butatone (MEK), methanol, methyl tert-butyl ether, N-butanol, N-propyl alcohol and isopropanol, propanols, propionaldehde, propyl ether, tert-amyl alcohol, tertiary amyl methyl ether (TAME), and valeraldehyde.

13. The method of claim 2, wherein, the non-magnetic mixed metal oxide, hydroxide, and oxyhydroxide sorbent nanomaterial includes a crystalline structure containing the metal in at least two oxidation states; an amount of the non-magnetic mixed metal oxide, hydroxide, and oxyhydroxide in crystalline structure being less than that of the amorphous non-crystalline structure.

14. The method of claim 2, wherein, the passing through the vessel occurs in a temperature range of ambient to 250° F.

15. The method of claim 2, wherein, the hydrocarbon process stream is a gas or liquid hydrocarbon stream including at least one hydrocarbon in a range of C2 up to a boiling point of 450° F.

16. The method of claim 2, wherein, the non-magnetic mixed metal oxide, hydroxide, and oxyhydroxide sorbent nanomaterial has a surface are in a range of 200 $m^2/g$ to 350 $m^2/g$.

17. The method of claim 1, wherein, the non-magnetic mixed metal oxide, hydroxide, and oxyhydroxide sorbent nanomaterial includes a crystalline structure containing the metal in at least two oxidation states; an amount of the non-magnetic mixed metal oxide, hydroxide, and oxyhydroxide in crystalline structure being less than that of the amorphous non-crystalline structure.

18. The method of claim 1, wherein, the passing through the vessel occurs in a temperature range of ambient to 250° F.

19. The method of claim 1, wherein, the hydrocarbon process stream is a gas or liquid hydrocarbon stream including at least one hydrocarbon in a range of C2 up to a boiling point of 450° F.

20. The method of claim 1, wherein, the non-magnetic mixed metal oxide, hydroxide, and oxyhydroxide sorbent nanomaterial has a surface are in a range of 200 $m^2/g$ to 350 $m^2/g$.

21. A method for reducing a oxygenate content of a hydrocarbon process stream containing an oxygenate an including a hydrocarbon in a range of C2 up to a boiling point of 450° F., the method comprising:

passing a liquid hydrocarbon process stream through a vessel containing a non-magnetic mixed metal oxide, hydroxide, and oxyhydroxide sorbent nanomaterial and operating in a temperature range of ambient to 250° F.;

the non-magnetic mixed metal oxide, hydroxide, and oxyhydroxide sorbent nanomaterial having an amorphous non-crystalline structure and a surface area in a range of 200 $m^2/g$ to 350 $m^2/g$;

the liquid hydrocarbon process stream having a first oxygenate content when entering the vessel and a second lower oxygenate content when exiting the vessel.

22. The method of claim 21, wherein, the reducing of the oxygenate content occurs on a surface area provided by the non-magnetic mixed metal oxide, hydroxide, and oxyhydroxide sorbent nanomaterial.

* * * * *